(12) United States Patent
Vasandani et al.

(10) Patent No.: US 11,622,700 B2
(45) Date of Patent: Apr. 11, 2023

(54) WEARABLE RESPIRATORY ENERGY HARVESTER

(71) Applicant: UNIVERSITY OF PITTSBURGH—OF THE COMMONWEALTH SYSTEM OF HIGHER EDUCATION, Pittsburgh, PA (US)

(72) Inventors: Paresh Vasandani, Pittsburgh, PA (US); Mingui Sun, Pittsburgh, PA (US); Wenyan Jia, Wexford, PA (US)

(73) Assignee: University of Pittsburgh-Of the Commonwealth System of Higher Education, Pittsburgh, PA (US)

( * ) Notice: Subject to any disclaimer, the term of this patent is extended or adjusted under 35 U.S.C. 154(b) by 0 days.

(21) Appl. No.: 17/660,238

(22) Filed: Apr. 22, 2022

(65) Prior Publication Data

US 2022/0240809 A1   Aug. 4, 2022

Related U.S. Application Data

(63) Continuation of application No. 16/339,477, filed as application No. PCT/US2017/056866 on Oct. 17, 2017, now Pat. No. 11,337,620.

(60) Provisional application No. 62/409,451, filed on Oct. 18, 2016.

(51) Int. Cl.
*A61B 5/08*   (2006.01)
*A61B 5/113*   (2006.01)
*A61B 5/00*   (2006.01)
*A61N 1/378*   (2006.01)
*A61N 1/372*   (2006.01)
(Continued)

(52) U.S. Cl.
CPC .............. *A61B 5/0816* (2013.01); *A61B 5/08* (2013.01); *A61B 5/1135* (2013.01); *A61B 5/6831* (2013.01); *A61N 1/372* (2013.01); *A61N 1/378* (2013.01); *A61B 5/002* (2013.01); *A61B 2560/0214* (2013.01); *A61N 1/3785* (2013.01); *H02J 7/32* (2013.01); *H04N 1/04* (2013.01)

(58) Field of Classification Search
CPC ....... A61B 5/0816; A61B 5/08; A61B 5/1135; A61B 5/6831; A61B 5/002; A61B 2560/0214; A61N 1/378; A61N 1/372; A61N 1/3785; H02J 7/32; H04N 1/04; H02N 1/00; H02N 1/002; H02N 1/004; H02N 1/006; H02N 1/008; H02N 1/04; H02N 1/06; H02N 1/08; H02N 1/10; H02N 1/12
USPC .................................................. 310/309, 310
See application file for complete search history.

(56) References Cited

U.S. PATENT DOCUMENTS 8,261,399 B2 *   9/2012   Wu ..................... A46B 15/0055
                                                             15/105

* cited by examiner

*Primary Examiner* — Ahmed Elnakib
(74) *Attorney, Agent, or Firm* — Nathaniel C. Wilks; Eckert Seamans Cherin & Mellott, LLC

(57) ABSTRACT

An energy harvesting device includes a housing (2), a moveable device (12) disposed within the housing and including a first surface including a first material (15) and a second surface including a second material (17), wherein the moveable device is operable to move to bring the first and second surfaces together and apart to cause contact and separation between the first and second materials, a first strap (4) attached to the housing, a second strap (6) coupled to the moveable device, wherein movement of the second strap causes operation of the moveable device, and elec-
(Continued)

tronic circuitry (20) structured to harvest energy from the electrical charge generated by the contact between the first and second materials.

20 Claims, 15 Drawing Sheets

(51) Int. Cl.
*H02J 7/32* (2006.01)
*H04N 1/04* (2006.01)

WEARABLE RESPIRATORY ENERGY HARVESTER

CROSS-REFERENCE TO RELATED APPLICATIONS

This is a continuation application which claims priority from U.S. patent application Ser. No. 16/339,477, filed on Apr. 4, 2019, entitled "WEARABLE RESPIRATORY ENERGY HARVESTER," which is a U.S. National Stage Application under 35 U.S.C. § 371 of PCT International Application No. PCT/US2017/056866, entitled "WEARABLE RESPIRATORY ENERGY HARVESTER," filed on Oct. 17, 2017, which claims priority under 35 U.S.C. § 119(e) from U.S. provisional patent application No. 62/409,451, entitled "WEARABLE RESPIRATORY ENERGY HARVESTER," filed on Oct. 18, 2016, the contents of which are incorporated herein by reference.

BACKGROUND OF THE INVENTION

1. Field of the Invention

The present invention generally relates to the energy harvesting devices and, more particularly, to energy harvesting devices for harvesting energy from respiration.

2. Description of the Related Art

The need to recharge and eventually replace batteries is increasingly significant for operating a variety of wearable electronic devices. Advances in low power design has brought down the energy requirements of wearable electronic devices and wireless sensor networks to the scale of microwatts and milliwatts, making human biomechanical energy harvesting a promising clean alternative to electrical power supplied by batteries. Human biomechanical energy harvesting generally refers to converting mechanical energy available from various sources in the human body to electrical energy. Respiration is a unique form of spontaneous and stable source of human biomechanical energy that has the potential to be converted to a sustainable power source for low power wearable electronic devices and integrated body sensor networks.

Respiratory energy can be harvested and converted to electricity from: (a) flow of air, and (b) abdomen/chest motion. Current techniques to harvest respiratory energy either require a face-mask or are invasive, thus limiting real-life applications. For utilizing energy from respiration to power wearable electronics, a non-invasive and comfortable approach is desirable.

SUMMARY OF THE INVENTION

In accordance with an aspect of the disclosed concept, an energy harvesting device comprises: a housing; a moveable device disposed within the housing and including a first surface including a first material and a second surface including a second material, wherein the moveable device is operable to move to bring the first and second surfaces together and apart to cause contact and separation between the first and second materials; a first strap attached to the housing; a second strap coupled to the moveable device, wherein movement of the second strap causes operation of the moveable device; and electronic circuitry structured to harvest energy from the electrical charge generated by the contact between the first and second materials.

In accordance with another aspect of the disclosed concept, an energy harvesting device comprises: a moveable device including a first surface including a first material and a second surface including a second material, wherein the moveable device is operable to move to bring the first and second surfaces together and apart to cause contact and separation between the first and second materials; and electronic circuitry structured to harvest energy from the electrical charge generated by the contact between the first and second materials, the electronic circuitry including: power management circuitry structured to condition the electrical charge generated by the contact between the first and second materials, wherein the power management circuitry includes a switch electrically connected to an output of the moveable device and being configured to cyclically open and close; and an energy storage device structured to store the conditioned electrical charge.

BRIEF DESCRIPTION OF THE DRAWINGS

A full understanding of the disclosed concept can be gained from the following description of the preferred embodiments when read in conjunction with the accompanying drawings in which.

DETAILED DESCRIPTION OF EXEMPLARY EMBODIMENTS

Figure 1:
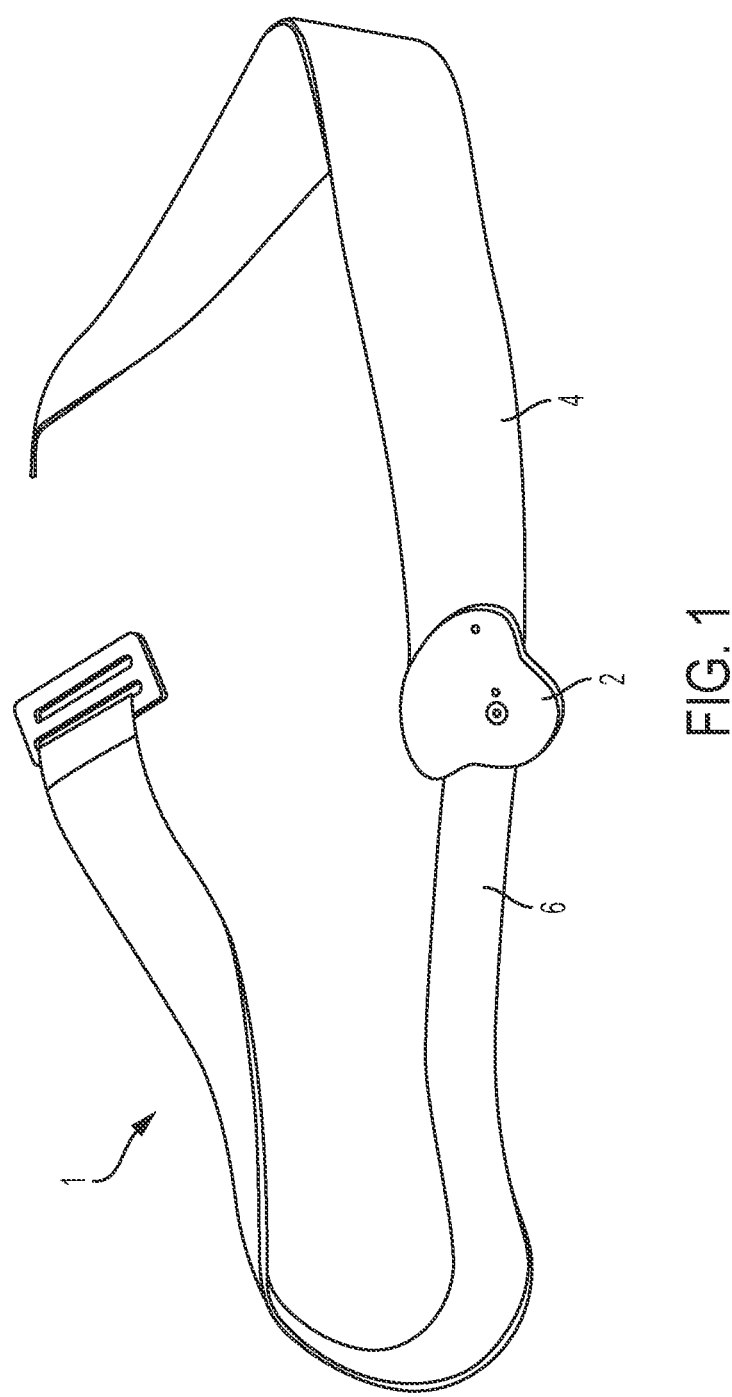
FIG. 1 is a view of an energy harvesting device in accordance with an example embodiment of the disclosed concept.

As used herein, the singular form of "a", "an", and "the" include plural references unless the context clearly dictates otherwise. As used herein, the statement that two or more parts or components are "coupled" shall mean that the parts are joined or operate together either directly or indirectly, i.e., through one or more intermediate parts or components, so long as a link occurs.

As used herein, "directly coupled" means that two elements are directly in contact with each other.

As used herein, "fixedly coupled" or "fixed" means that two components are coupled so as to move as one while maintaining a constant orientation relative to each other.

As used herein, the word "unitary" means a component is created as a single piece or unit. That is, a component that includes pieces that are created separately and then coupled together as a unit is not a "unitary" component or body.

As used herein, the statement that two or more parts or components "engage" one another shall mean that the parts exert a force against one another either directly or through one or more intermediate parts or components.

As used herein, the term "number" shall mean one or an integer greater than one (i.e., a plurality).

Directional phrases used herein, such as, for example and without limitation, top, bottom, left, right, upper, lower, front, back, and derivatives thereof, relate to the orientation of the elements shown in the drawings and are not limiting upon the claims unless expressly recited therein.

The present invention will now be described, for purposes of explanation, in connection with numerous specific details in order to provide a thorough understanding of the subject invention. It will be evident, however, that the present invention can be practiced without these specific details without departing from the spirit and scope of this innovation.

In a human respiratory cycle, the chest and/or abdomen expands during inhalation and then retracts during exhalation. The cycle of motion is consistent and quite predictable. A typical person breathes approximately 18 times per minute. While the number of breaths per minute may vary somewhat, there are generally no extended breaks between breaths. In other words, the respiratory cycle creates a continuous in and out mechanical motion, thereby providing a continuous source of mechanical energy that can be converted to electrical energy.

Exemplary embodiments of the disclosed concept generate electrical power from the mechanical motion of the respiratory cycle. For example, in some example embodiments of the disclosed concept, the triboelectric effect and electrostatic induction are used to convert the mechanical motion of the respiratory cycle into electrical power. The triboelectric effect is when contact between two materials that differ in polarity of charge separation yields surface charge transfer. Electrostatic induction is a redistribution of electrical charge in an object caused by the influence of nearby charges. Periodic contact and separation of the oppositely charged surfaces can create a dipole layer and induce a potential drop, which drives the flow of electrons through an external circuit in response to a mechanical agitation. This creates an alternating current (AC) output in the external circuit. In some example embodiments of the disclosed concept, the mechanical motion of the respiratory cycle is used to cyclically bring two materials together and apart to create an AC output. This AC energy is converted to direct current (DC) energy using a rectifier and the energy is then stored in an electrical storage device, such as a battery, a capacitor, or a supercapacitor, which can then be used to power electronic devices.

Figure 2:
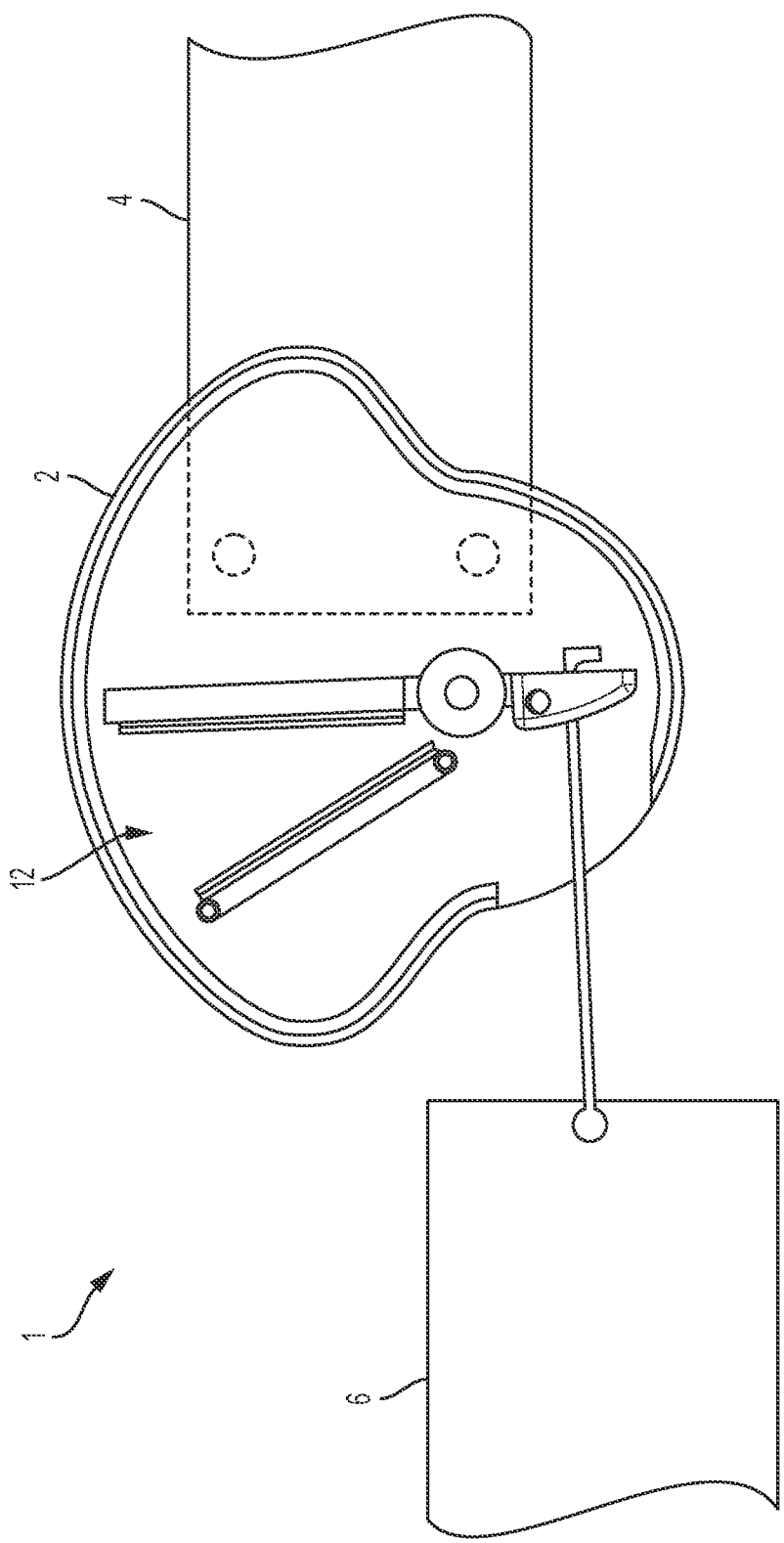
FIGS. 2 and 3 are views of the energy harvesting device of FIG. 1 with its cover removed.
Figure 3:
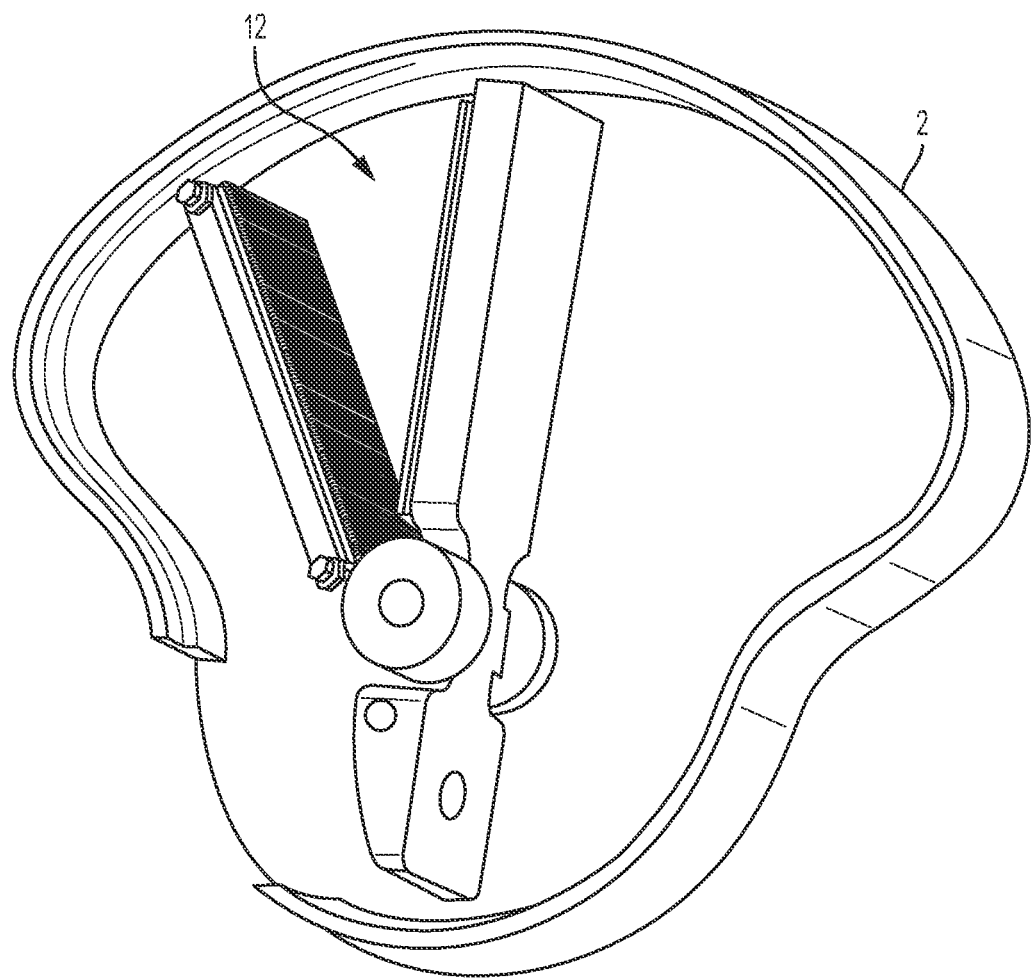
Figure 4:
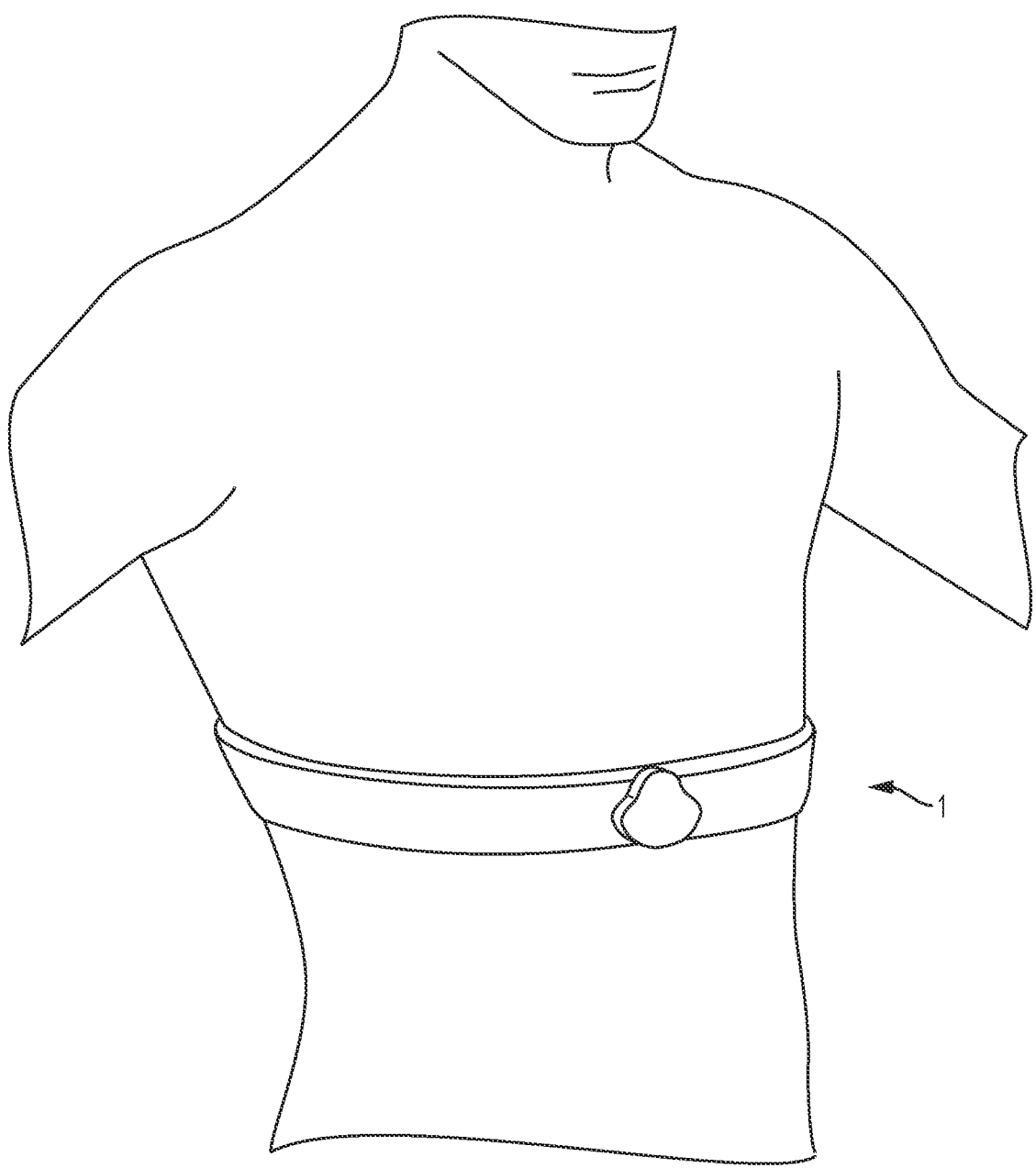
FIG. 4 is a view of the energy harvesting device of FIG. 1 employed in use on a person.

FIG. 1 is a view of an energy harvesting device 1 in accordance with an example embodiment of the disclosed concept. FIGS. 2 and 3 are additional views of the energy harvesting device 1 of FIG. 1 with a housing cover removed, and FIG. 4 is a view of the energy harvesting device 1 of FIG. 1 while worn by a person.

The energy harvesting device 1 includes a housing 2 and straps 4, 6. As shown in FIGS. 2 and 3, the energy harvesting device 1 also includes a moveable device 12 disposed inside the housing 2. The housing 2 is composed of a front housing and a rear housing that attach to each other to enclose the moveable device 12. The energy harvesting device 1 further includes electronic circuitry 20 (shown in FIG. 7).

The straps 4,6 include a fixed strap 4 that is attached to the housing 2 (e.g., attached to a rear side of the housing) and a movable strap 6 that is attached to the moveable device 12. When the energy harvesting device 1 is worn by a person, such as is shown in FIG. 4, the motion caused by the person inhaling causes the movable strap 6 to pull on the moveable device 12 and cause the moveable device 12 to open. The moveable device 12 is biased to the closed position, so when the person exhales, tension from the movable strap 6 on the moveable device 12 is lessened and the moveable device 12 closes. The moveable device 12 cycles between the open and closed position with each respiratory cycle of the person.

Figure 5A:
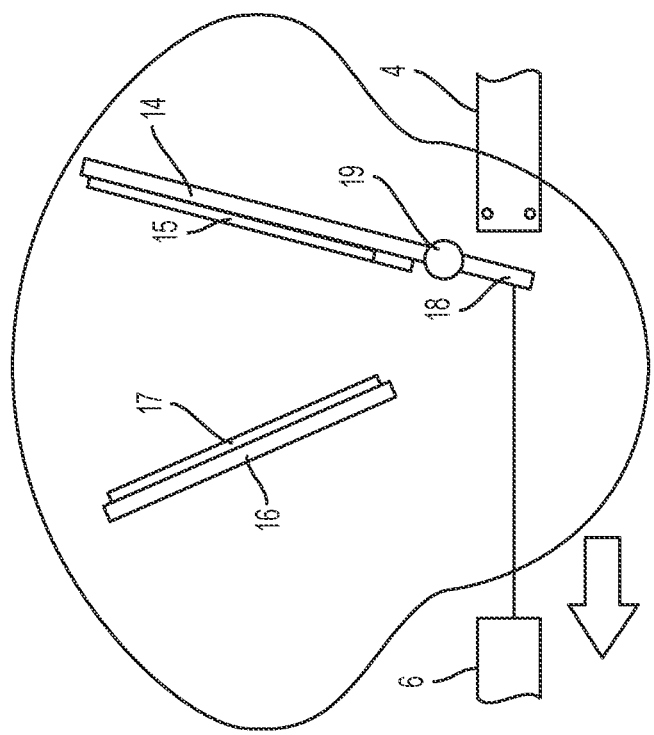
FIGS. 5A and 5B are schematic diagrams of a moveable device in operation in accordance with an example embodiment of the disclosed concept.
Figure 5B:
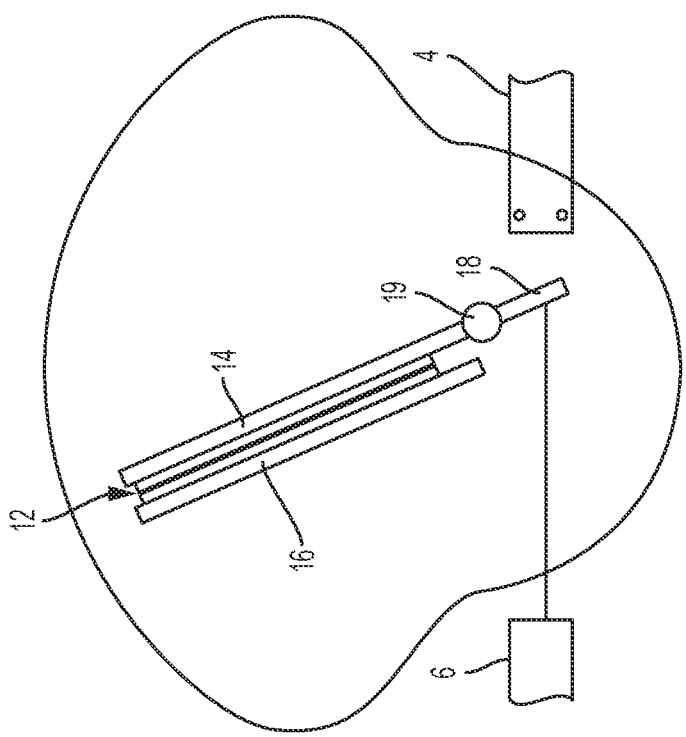

FIGS. 5A and 5B illustrate the operation of the moveable device 12 in more detail. FIG. 5A illustrates the moveable device 12 in the closed position (i.e., the position the moveable device 12 would be in when the person finishes exhaling). FIG. 5B illustrates the moveable device 12 in the open position (i.e., the position the moveable device 12 would be in when the person finished inhaling). As shown in FIGS. 5A and 5B, the moveable device 12 includes a movable member 14 and a fixed member 16. The moveable device 12 also includes a lever arm 18 that is attached to the movable strap 6. The lever arm 18 and the movable member 14 are attached to a hinge 19 and move in conjunction with each other about the hinge 19. The hinge 19 may include a recoil or retreating member such as a spring or an elastic band that biases the moveable device 12 to the closed position.

In some example embodiments of the disclosed concept, a first material 15 is attached to the surface of the movable member 14 facing the fixed member 16 and a second material 17 is attached to the surface of the fixed member 16 facing the movable member 14. Table 1 is a triboelectric series table listing materials that are arranged according to their tendency of gaining or losing electrons.

TABLE 1

Rabbit's Fur, Hair
Glass
Mica
Wool
Nylon
Silk
Paper
Wood
Amber
Rubber Balloon
Nickel
Copper
Silver
Gold
Polystyrene
Acrylic
Polyvinyl chloride
Polyethylene
Polypropylene
Teflon (PTFE)

A material towards the bottom of the series, when touched to a material near the top of the series, will acquire a negative charge. The farther away two materials are from each other on the series, the greater the charge transferred. For example, when silk and acrylic are brought into contact, the contact will create an electrical charge due to the triboelectric effect. Benefits may be seen when the first and second materials 15,17 have larger separation on the triboelectric series When the first and second materials 15,17 are brought into contact due to the motion of the moveable device 12 caused by the mechanical motion of respiration, the surfaces of the first and second materials 15,17 will take on opposite static charges with equal density, as a result of contact electrification or triboelectric effect. Electrodes 18,19 (shown in FIG. 6) are attached to the first and second materials 15,17 in order to capture the generated electrical charge. In some example embodiments, electrodes 18,19 are attached to both of the first and second materials 15,17. However, in some example embodiments an electrode is attached to only one of the first and second materials 15,17. While silk and acrylic are examples of two materials having contact electrification associated with opposite charges, it will be appreciated by those having ordinary skill in the art that any materials having contact electrification associated with opposite charges may be employed as the first and second materials 15,17 without departing from the scope of the disclosed concept.

Figure 6:
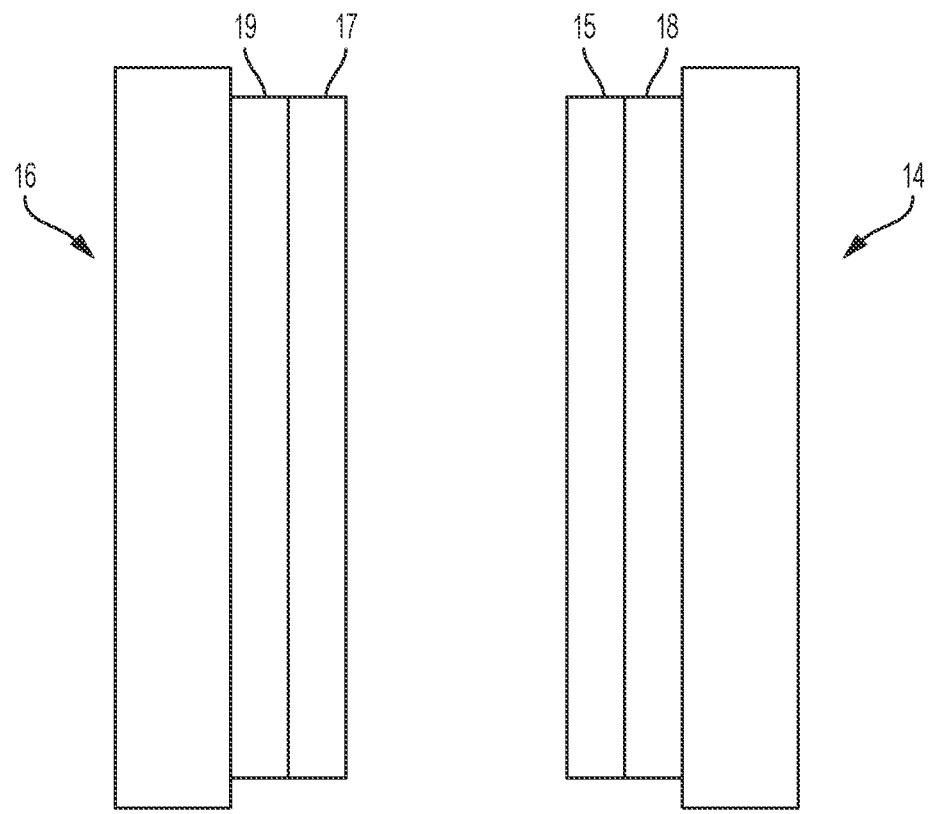
FIG. 6 is a cross-section view of moveable and fixed members of a moveable device in accordance with an example embodiment of the disclosed concept.

FIG. 6 is a cross-section view showing an example of the movable member 14 and a fixed member 16. As shown in FIG. 6, the electrodes 18,19 and the first and second materials 15,17 may be layered on the moveable 14 and fixed members 16, respectively.

In some example embodiments of the disclosed concept, the first material 15 is a polyethylene terephthalate (PET) film (e.g., without limitation, 15 mm×25 mm; 0.05 mm thick) and the second material 17 is a polydimethylsiloxane (PDMS) film (e.g., without limitation, 15 mm×25 mm; 0.05 mm thick). The electrodes 18,19 are composed of, for example and without limitation, copper or another conductive material deposited on the moveable and fixed members 14,16 and the first and second materials 15,17 are applied to the electrodes 18,19. While in some example embodiments, a PET file is employed as the first material 15 and a PDMS film is employed as the second material 17, it will be appreciated that other materials may be employed without departing from the scope of the disclosed concept.

In some example embodiments of the disclosed concept, the first and/or second material 15,17 may have patterned surfaces (e.g., without limitation, micro-patterned surfaces). The patterned surfaces increase the actual contact area, thereby increasing the surface charge density of the first and second materials 15,17, resulting in an increased output voltage of the moveable device 12 compared with equivalent materials that have apparently smooth or flat surfaces, but are actually rough at a microscopic level. Therefore, the actual contact area is only a fraction of the apparent contact area. In some example embodiments of the disclosed concept, the first and/or second material 15,17 may have a domed-structure such as a microdomed structure (e.g., without limitation, a PDMS film having a microdome patterned surface).

Figure 7:
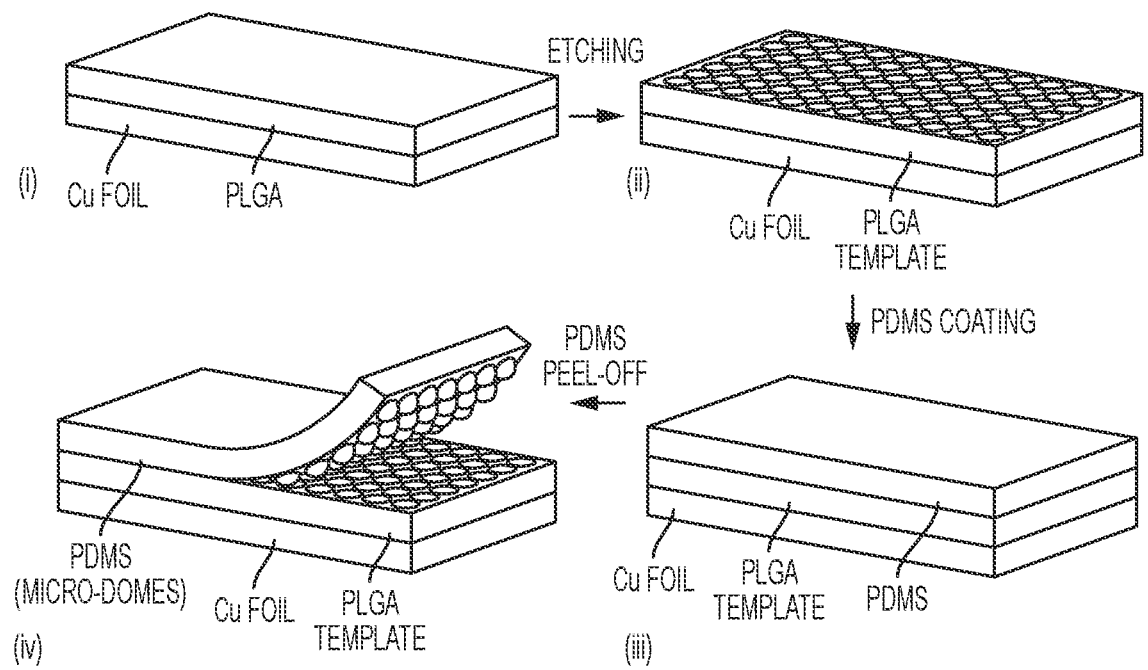
FIG. 7 is a diagram of a method of producing a film with a micro-domed surface structure in accordance with an example embodiment of the disclosed concept.

An example of forming a PDMS film having a microdome patterned surface is shown in FIG. 7. The example if FIG. 7 is based on a polylactic acid (PLA) patterning technique used in hybrid supercapacitors. A microwell patterned template is first created as a mold for making PDMS film with regularly ordered microdome structures, thus eliminating the need for using traditional photolithography technique to create a patterned silicon wafer mold. Like PLA, a Poly Lactic-co-Glycolic Acid (PLGA) polymer thin film of appropriate thickness on copper foil self-assembles into well-ordered arrays of microwell structures with dimensions of approximately 5 µm after being etched in a chloroform and methanol mixture, thus forming a PLGA template (shown in FIG. 7(ii)). Thereafter, a PDMS mixture is coated onto the PLGA template, allowed to cure (shown in FIG. 7(iii)), and peeled-off. The result is a PDMS film with regularly ordered microdome structures (shown in FIG. 7(iv)). The microwell structures are created because etching induces micro-phase separation of the PLGA film in the mixture. The capillary action during evaporation of chloroform causes the PLGA film to assemble into close-packed array on the foil. The consequent exchange of solvent and non-solvent is responsible for micro-phase separation in the polymer solution. The spongy cellular structure is created due to the liquid-liquid demixing by nucleation and growth of a polymer-poor phase. To obtain patterns with a constant spongy morphology, the phase separation process is stalled before completion. A PDMS film with regularly ordered microdome structures formed in the manner shown in FIG. 7 may be employed as the first and/or second materials 15,17. However, it will be appreciated by those having ordinary skill in the art that other materials, or similar materials formed by different processes, may be employed as the first and/or second materials 15,17 without departing from the scope of the disclosed concept.

Figure 8:
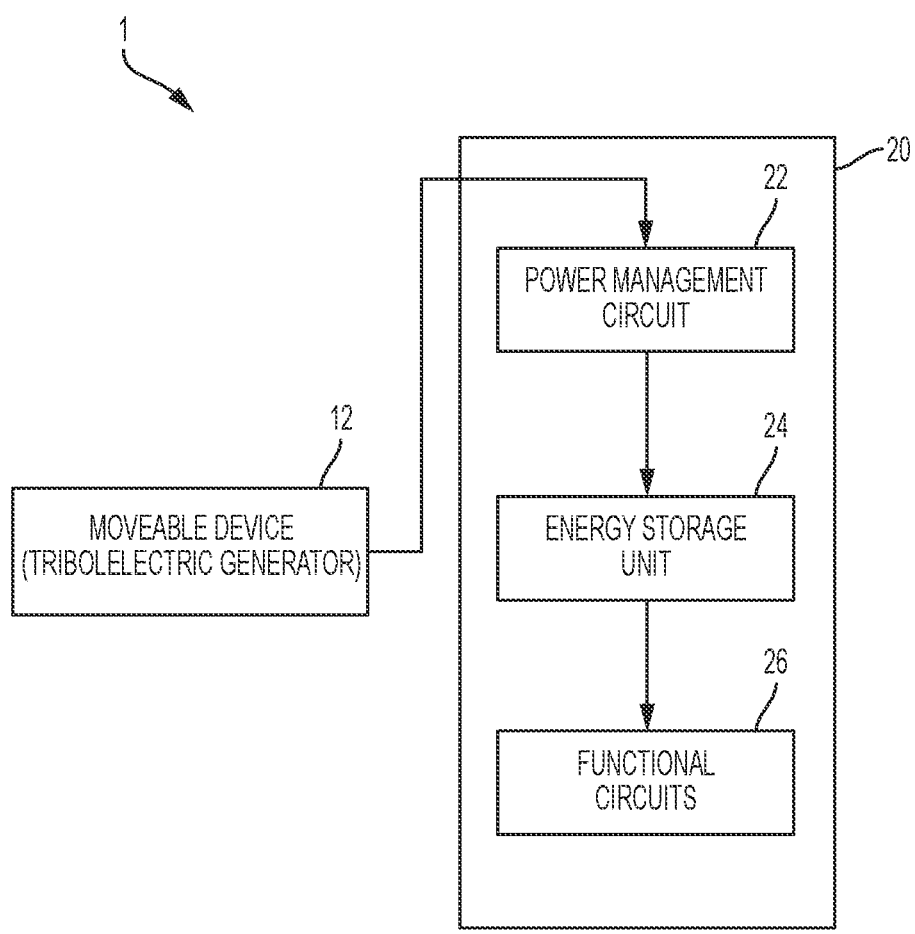
FIG. 8 is a schematic diagram of an energy harvesting device in accordance with an example embodiment of the disclosed concept.

FIG. 8 is a schematic diagram of the energy harvesting device 1 in accordance with some example embodiments of the disclosed concept. The energy harvesting device 1 includes the previously described moveable device 12 which operates as a triboelectric generator. The energy harvesting device 1 includes electronic circuitry 20 (not shown in FIGS. 1-4) including a power management circuit 22, an energy storage unit 24, and functional circuits 26.

The power management circuit 22 is electrically connected to the electrodes of the moveable device 12 and receives the electrical charge generated by the moveable device 12. The power management circuit 22 includes circuitry to convert the electrical charge generated by the moveable device 12 to a form suitable to charge the energy storage unit 24. The power management circuit 22 may include, for example, one or more rectifiers, capacitors, switches, capacitors, integrated circuits, or other electrical components suitable to perform one or more of rectification, voltage regulation, smoothing, AC/DC conversion, or other functions for converting electrical charge.

The energy storage unit 24 may be any type of device suitable for storing electrical energy. For example and without limitation, the energy storage unit 24 may be a rechargeable battery. However, one having ordinary skill in the art will appreciate that the energy storage unit 24 may be composed of other components capable of storing electrical energy such as, for example and without limitation, a capacitor.

The functional circuits 26 may be any circuitry that utilizes the energy stored in the energy storage unit 24. For example and without limitation, in some example embodiments of the disclosed concept, the functional circuits 26 include circuitry that provides for processing and communication of data associated with the breathing of a person wearing the energy harvesting device 1. However, it will be appreciated by those having ordinary skill in the art that the functional circuits 26 may perform any other type of function without departing from the scope of the disclosed concept.

Figure 9:
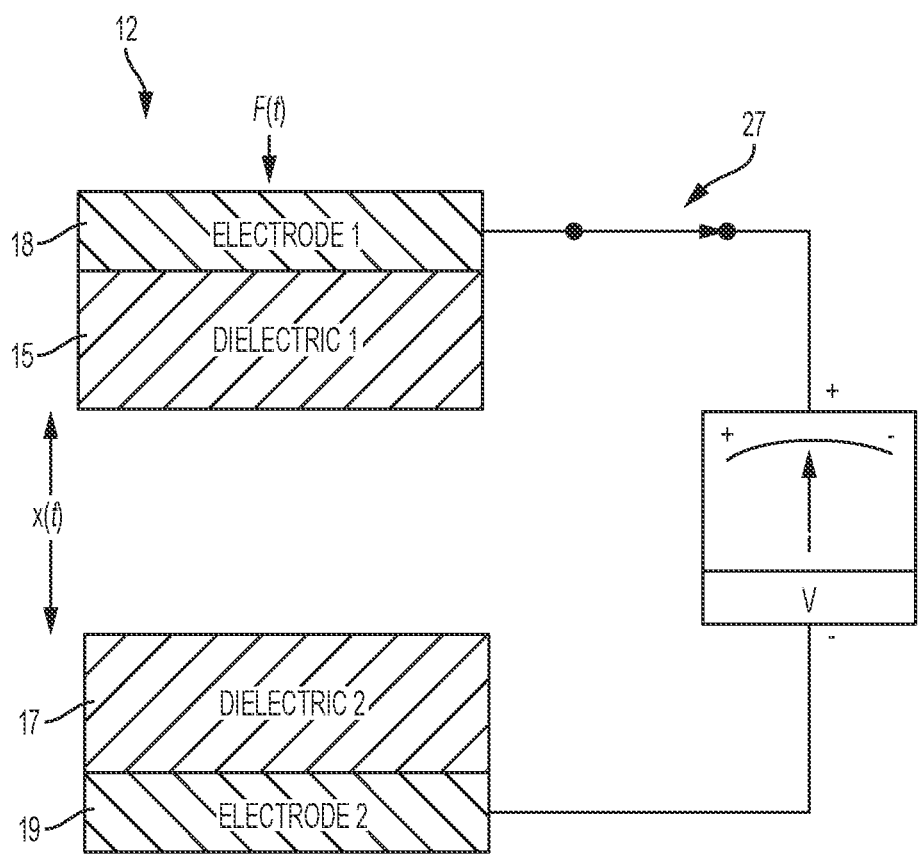
FIG. 9 is a structural diagram including a switch in accordance with an example embodiment of the disclosed concept.
Figure 10:
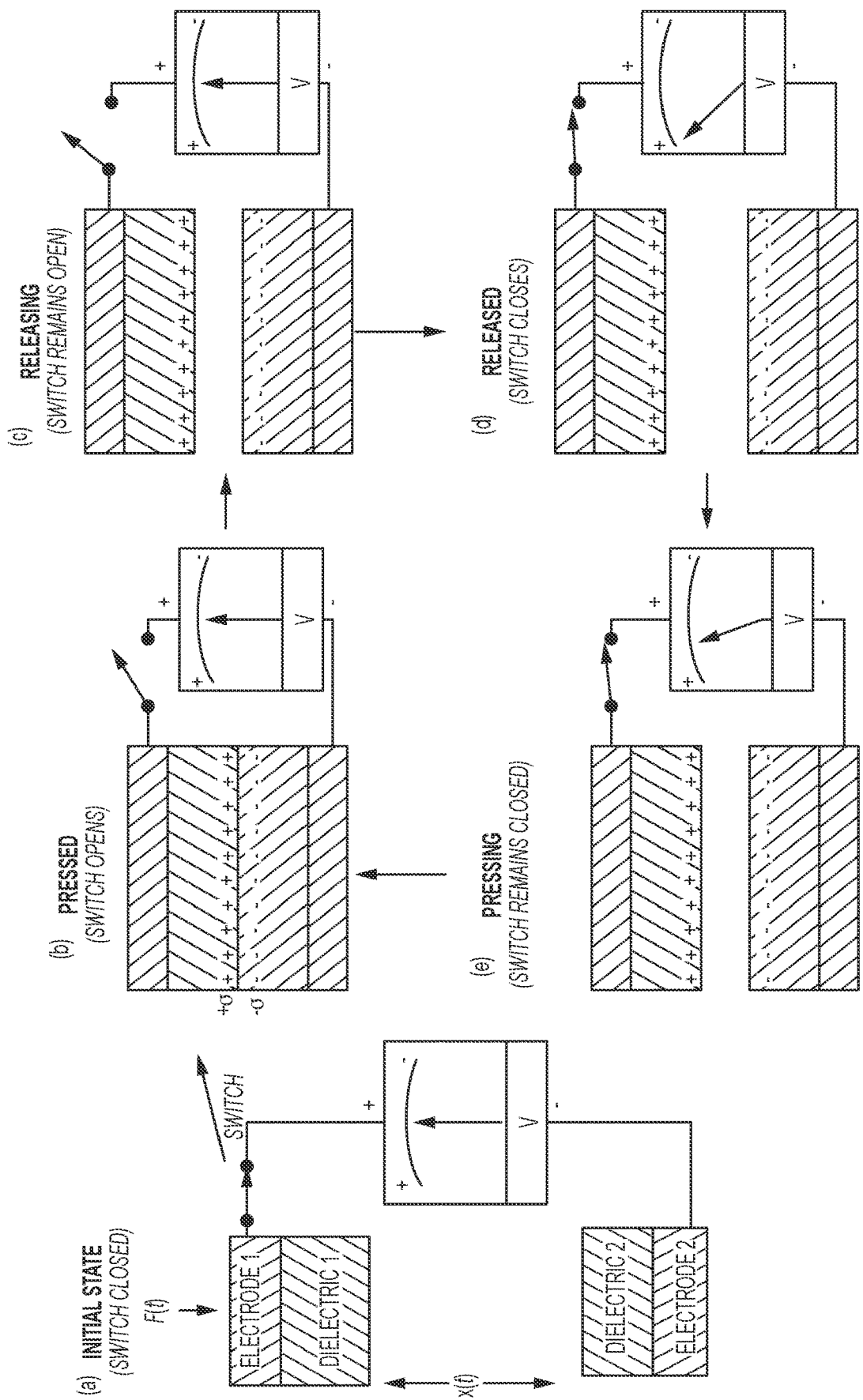
FIG. 10 is a structural diagram showing operation of the switch of FIG. 9.

FIG. 9 is a structural diagram including a switch in accordance with an example embodiment of the disclosed concept and FIG. 10 is a structural diagram showing operation of the switch of FIG. 9. In some example embodiments, the electronic circuitry 20 includes a switch 27. The switch 27 is electrically connected to an output of the moveable device 12. The switch 27 is configured to open and close. The switch 27 may be an electrically controlled switch (e.g., without limitation, a relay) or a mechanically controlled switch. Opening the switch 27 causes the moveable device 12 to be electrically disconnected from the energy storage unit 24 and closing the switch 27 causes the moveable device 12 to be electrically connected to the energy storage unit 24.

In some example embodiments of the disclosed concept, the switch 27 is opened and closed at a predetermined frequency (e.g., without limitation, 1 Hz). It will be appreciated that any suitable frequency may be selected. In some example embodiments of the disclosed concept, the switch 27 is driven synchronously with the movement of the moveable device 12. FIG. 10 shows an example of synchronous operation. For example, the switch opens when the first and second materials 15,17 are pressed together. The switch 27 then closes when the first and second materials 15,17 are their furthest apart (shown in FIG. 10(d)). The process repeats for each opening and closing of the moveable device 12. For example, if the moveable device 12 opens and closes at a frequency of 1 Hz, the switch 27 will open and close at the same frequency.

Including the switch 27 increases the effectiveness of the energy harvesting device 1. For example, typical triboelectric nanogenerators would directly connect the output of the nanogenerator to an energy storage device. In the presently disclosed concept, it has been found that including the switch 27 and operating the switch at a predetermined frequency or synchronously with the moveable device 12 increase the output voltage of the moveable device 12 and increases the amount of voltage stored in the energy storage unit 24 over a span of time compared to if the switch 27 were omitted. For example, including and operating the switch 27 at the output of the moveable device 12 increases the peak-to-peak output voltage of the moveable device 12, which increases how quickly energy can be stored in the energy storage unit 24.

Figure 11:
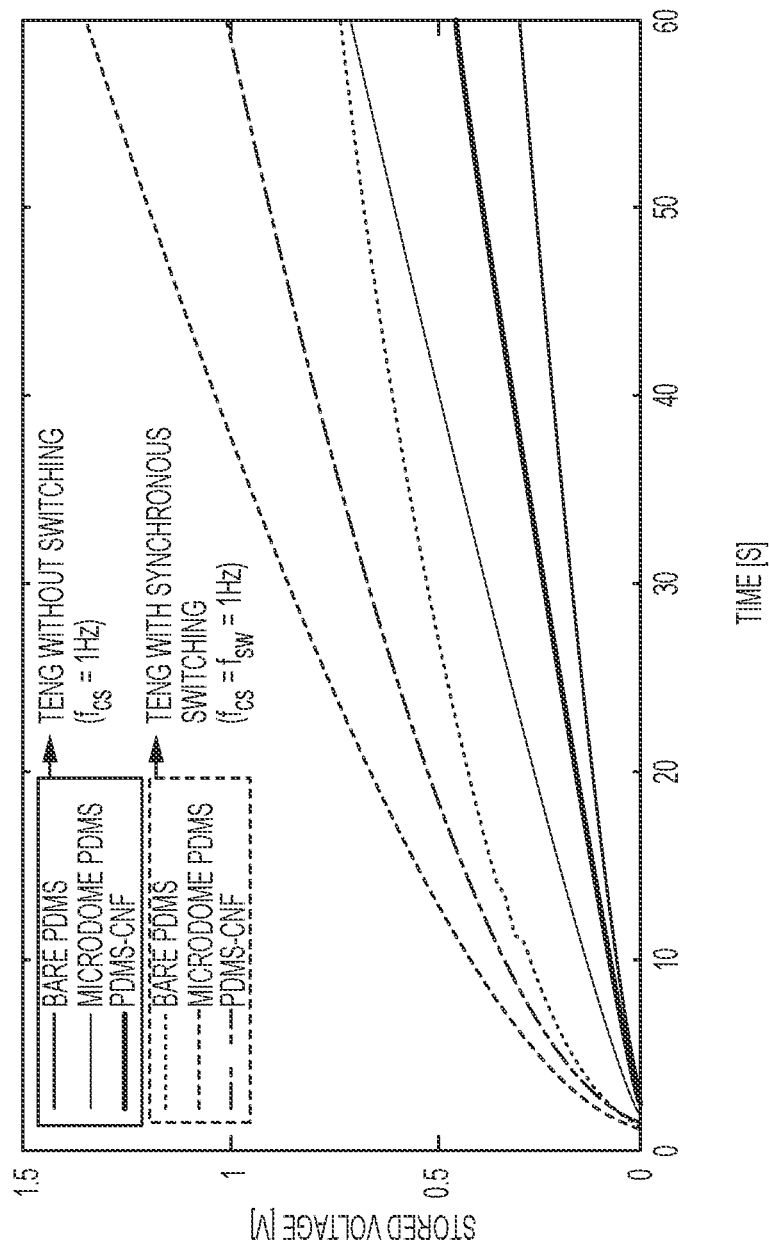
FIG. 11 is a graph showing the results of employing a switch in accordance with an example embodiment of the disclosed concept.

FIG. 11 is a chart showing the compared stored voltage of different types of moveable devices used with or without the switch 27. In particular, FIG. 11 compares the resultant stored voltages over time when the second material 17 is bare PDMS (e.g., PDMS without a micro-pattern formed in it), PDMS having a microdomed pattern, and PDMS-CNF (polydimethylsiloxane—carbon nanofiber). The PDMS-CNF is a composite material of CNFs in a PDMS base. In FIG. 11, the $f_{cs}$ represents the contact-separation frequency of the moveable device 12 and $f_{sw}$ represents the switching frequency of the switch 27. Furthermore, the resultant stored voltage over time for these three variations are compared without the use of the switch 27 and with the switch being drive synchronously with the moveable device 12. As shown in FIG. 11, using the switch 27 and driving it synchronously with the moveable device 12 results in about double the amount of voltage being stored in the energy storage unit 24 over a span of time compared to not using switching. Including the switch 27 has also been found to reduce the optimal load resistance associated with the electronic circuitry 20.

Figure 12:
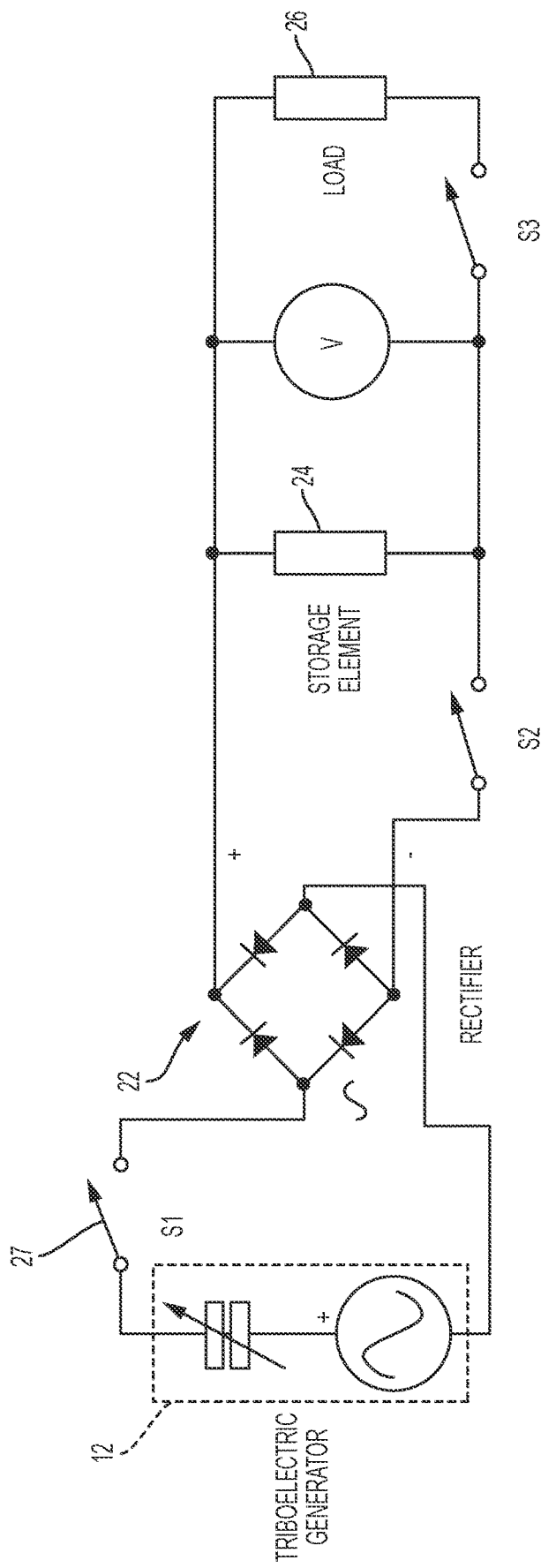
FIG. 12 is a diagram of electronic circuitry that may be included in energy harvesting devices in accordance with various embodiments of the disclosed concept.

FIG. 12 is a circuit diagram of the moveable device 12 and electronic circuitry 20 in accordance with an example embodiment of the disclosed concept. As shown in FIG. 8, the power management circuit 22 includes a rectifier and switches and is disposed between the moveable device 12 and the energy storage unit 24. The power management circuit 22 is structured to convert AC power output by the moveable device 12 to DC power and use it to charge the energy storage device 24. The functional circuits 26 are shown generally as a load that is arranged to use power stored in the energy storage device 24. While FIG. 12 illustrates one example of circuitry that may be used in the energy harvesting device 1, it will be appreciated that other circuits and components may be employed without departing from the scope of the disclosed concept. For example and without limitation, one having ordinary skill in the art would understand that various different types and arrangements of circuit may be employed in the power management circuit 22 without departing from the scope of the disclosed concept. It will be appreciated by those having ordinary skill in the art that other components and arrangements of components may be employed in the electronic circuitry 20 without departing from the scope of the disclosed concept.

Figure 13:
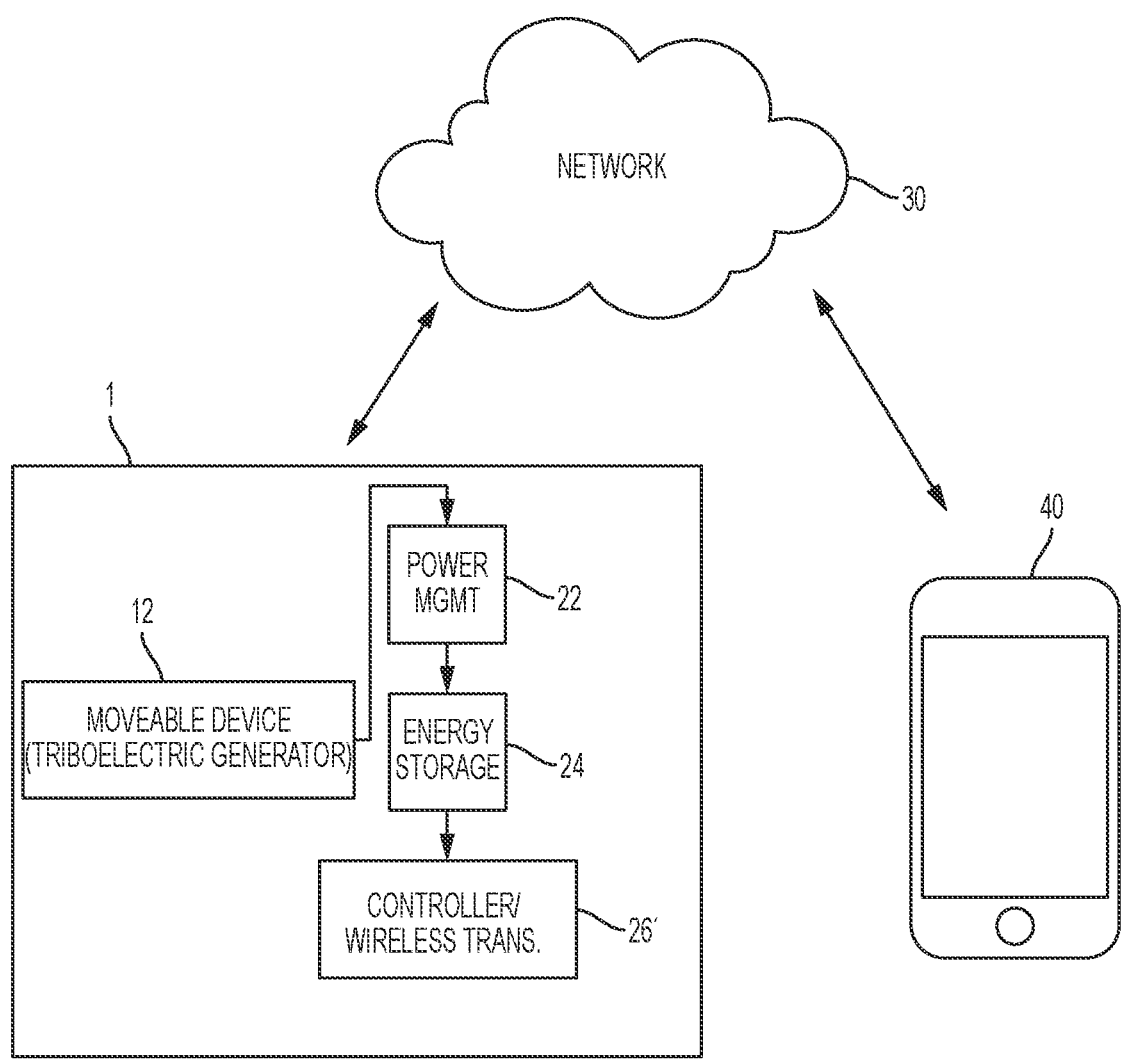
FIG. 13 is a schematic diagram of a system for sensing breathing in accordance with an example embodiment of the disclosed concept.

In some example embodiments of the disclosed concept, the energy harvesting device 1 is employed as a breathing sensor. FIG. 13 is a schematic diagram of a system that utilizes the energy harvesting device 1 in accordance with an example embodiment of the disclosed concept as a breathing sensor. In addition to harvesting energy from the mechanical motion of respiration, the moveable device 12 is able to sense breaths (e.g., frequency of breaths) and the deepness of breaths since its motion is based on the mechanical motion of the person wearing the device. In accordance with this embodiment of the disclosed concept, the functional circuits in the energy harvesting device 1 include control circuitry (e.g., without limitation, a processor and memory) and wireless transmission circuitry 26'. The processor may be, for example and without limitation, a microprocessor (μP), a microcontroller, or some other suitable processing device, that interfaces with the memory. The memory can be any one or more of a variety of types of internal and/or external storage media such as, without limitation, RAM, ROM, EPROM(s), EEPROM(s), FLASH, and the like that provide a storage register, i.e., a machine readable medium, for data storage such as in the fashion of an internal storage area of a computer, and can be volatile memory or nonvolatile memory. The memory may have stored therein a number of routines that are executable by the processor. It is also contemplated that the control circuitry may implement its functionality without a processor and/or memory.

The control circuitry and wireless transmission circuitry 26' are able to obtain information on a person's breathing from the motion of the moveable device 12 (e.g., without limitation, outputs of charge from the moveable device 12 may be an indication of completion of a breath) and process and wirelessly output the information. The energy harvesting device 1 may be included in a system including a network 30 (e.g., without limitation, a Wi-Fi network or any other suitable network) and an external device 40 (e.g., without limitation, a smart phone, a computer, or any other suitable electronic device). The external device 40 may include an application or other software that can process and display information about the person's breathing based on the information received from the energy harvesting device 1.

Since the energy harvesting device 1 is worn around a person's chest or abdominal area, it is able to obtain accurate information about the person's breathing. In some example embodiments, two belts may be used to obtain the ratio of chest and abdomen motion during breathing. Additionally, since the energy harvesting device 1 is able to harvest electrical power from the mechanical motion of the person's respiratory cycle, the energy harvesting device 1 is able to power itself without the need to replace or recharge batteries from an external source.

Figure 14:
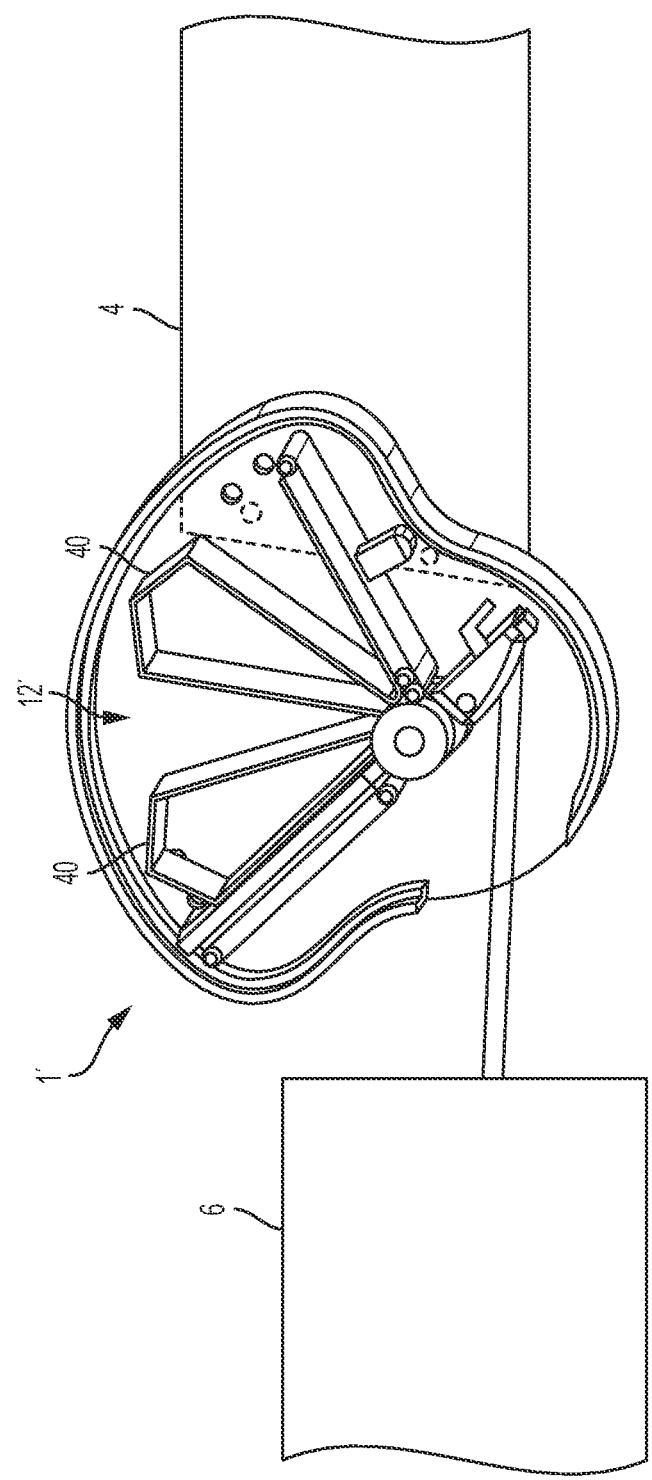
FIG. 14 is a schematic diagram of an energy harvesting device in accordance with another example embodiment of the disclosed concept.

It will be appreciated by those having ordinary skill in the art that variations may be made to the energy harvesting device 1 without departing from the scope of the disclosed concept. For example, FIG. 14 is a diagram of an energy harvesting device 1' in accordance with another example embodiment of the disclosed concept. In the example shown in FIG. 14, the moveable device 12' includes accordion-like structures 40. Material, such as the first and/or second materials 15,17 may be disposed on surfaces of the accordion-like structures 40. Movement of the moveable device 12' will cause multiple instances of surfaces of the accordion-like structures 40 coming into contact with each other, thus increasing the amount of electrical charge output by the moveable device 12'.

Figure 15:
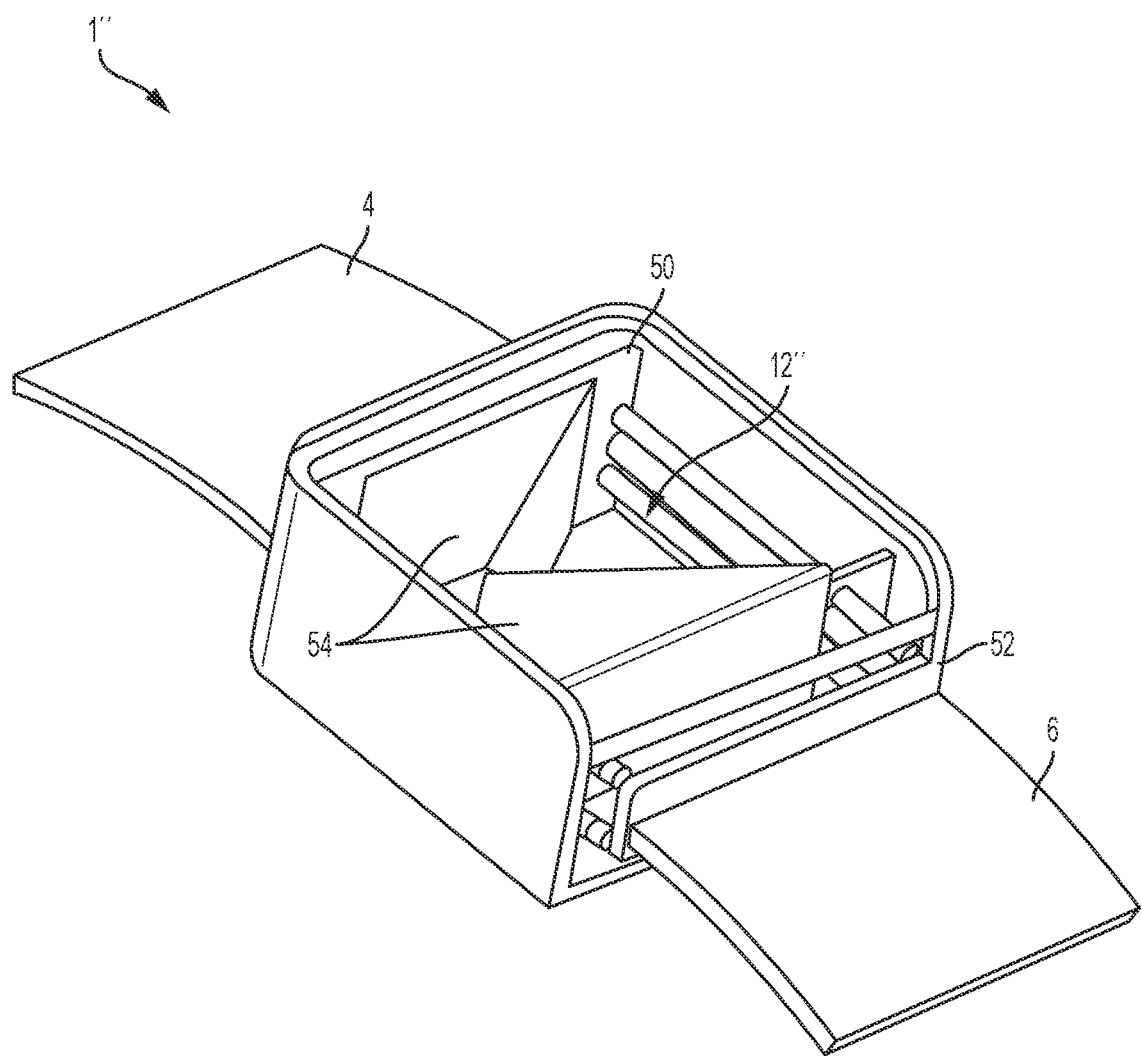
FIG. 15 is a schematic diagram of an energy harvesting device in accordance with another example embodiment of the disclosed concept.

Another example embodiment of an energy harvesting device 1" is shown in FIG. 15. In the example shown in FIG. 15, a sliding device 12" is used as the moveable device. The sliding device 12" includes a plate that is attached to strap 6 and slides in and out based on movement of the strap 6. The sliding movement causes zig-zag like structures of the sliding device 12" to come into contact and separate from each other. Surfaces of the zig-zag structure that face each other may be covered with the first and second materials, respectively. That is, when the zig-zag structure is compressed, surfaces that are covered with the first material 15 will come into contact with surfaces that are covered with the second material thus creating an electrical charge. The number of bends includes in the zig-zag structure will define how many surfaces come into contact with each other.

For example, the energy harvesting device 1" may include a fixed plate member 50 and a movable plate 52 member structured to move with respect to the fixed plate member 50 and being coupled to the strap 6. A zig-zag structure 54 is disposed between the fixed plate member 50 and the movable plate member 52. The zig-zag structure 54 is structured to compress when the movable plate member 52 moves toward the fixed plate member 50. The zig-zag structure 54 includes a first surface portion and a second surface portion facing the first surface portion. The first surface portion includes the first material and the second surface portion includes the second material.

In the claims, any reference signs placed between parentheses shall not be construed as limiting the claim. The word "comprising" or "including" does not exclude the presence of elements or steps other than those listed in a claim. In a device claim enumerating several means, several of these means may be embodied by one and the same item of hardware. The word "a" or "an" preceding an element does not exclude the presence of a plurality of such elements. In any device claim enumerating several means, several of these means may be embodied by one and the same item of hardware. The mere fact that certain elements are recited in mutually different dependent claims does not indicate that these elements cannot be used in combination.

Although the invention has been described in detail for the purpose of illustration based on what is currently considered to be the most practical and preferred embodiments, it is to be understood that such detail is solely for that purpose and that the invention is not limited to the disclosed embodiments, but, on the contrary, is intended to cover modifications and equivalent arrangements that are within the spirit and scope of the appended claims. For example, it is to be understood that the present invention contemplates that, to the extent possible, one or more features of any embodiment can be combined with one or more features of any other embodiment.

What is claimed is:

1. An energy harvesting device, comprising:
 a first surface including a first material;
 a second surface including a second material, wherein first and second surfaces are operable to move together and apart to cause contact and separation between the first and second materials; and
 electronic circuitry structured to harvest energy from an electrical charge generated by the contact between the first and second materials, the electronic circuitry including:
  power management circuitry structured to condition the electrical charge generated by the contact between the first and second materials, wherein the power management circuitry includes a switch configured to cyclically open and close; and
  an energy storage device structured to store the conditioned electrical charge, wherein the switch is electrically coupled between one of the first and second surfaces and the energy storage device.

2. The energy harvesting device of claim 1, wherein the power management circuitry is structured to control the switch to open and close at a predetermined frequency.

3. The energy harvesting device of claim 2, wherein the predetermined frequency is about 1 Hz.

4. The energy harvesting device of claim 1, wherein the power management circuitry is structured to control the switch to open and close synchronously with movement of the first and second surfaces.

5. The energy harvesting device of claim 4, wherein the power management circuitry is structured to control the switch to open when the first and second surfaces press together and to close when the first and second surfaces are furthest apart.

6. The energy harvesting device of claim 1, wherein the power management circuitry includes a rectifier structured to rectify the electrical charge generated by the contact between the first and second materials.

7. The energy harvesting device of claim 1, wherein the first material has a negative contact electrification charge and the second material has a positive contact electrification charge.

8. The energy harvesting device of claim 1, wherein at least one of the first and second materials is a patterned material or a composite material.

9. The energy harvesting device of claim 1, wherein the energy storage device is at least one of a rechargeable battery and a capacitor.

10. The energy harvesting device of claim 1, wherein the power management circuitry is structured to perform at least one of rectification, voltage regulation, smoothing, and AC/DC conversion to condition the electrical charge generated by the contact between the first and second materials.

11. An energy harvesting device, comprising:
 a first surface including a first material;

a second surface including a second material, wherein first and second surfaces are operable to move together and apart to cause contact and separation between the first and second materials, wherein an electrical charge is generated by contact between the first and second materials;

an energy storage device structured to store the electrical charge generated by contact between the first and second materials; and a switch electrically coupled between one of the first and second surfaces and the energy storage device, the switch being configured to cyclically open and close.

12. The energy harvesting device of claim 11, wherein the switch is configured to open and close at a predetermined frequency.

13. The energy harvesting device of claim 11, wherein the switch is configured to open and close synchronously with movement of the first and second surfaces.

14. The energy harvesting device of claim 13, wherein the switch is configured to open when the first and second surfaces press together and to close when the first and second surfaces are furthest apart.

15. The energy harvesting device of claim 11, wherein the first material has a negative contact electrification charge and the second material has a positive contact electrification charge.

16. The energy harvesting device of claim 11, wherein at least one of the first and second materials is a micropatterned material or a composite material.

17. The energy harvesting device of claim 11, wherein the energy storage device is at least one of a rechargeable battery and a capacitor.

18. A method of harvesting energy, the method comprising:

providing a first surface including a first material, a second surface including a second material, wherein an electrical charge is generated by contact between the first and second materials, an energy storage device structured to store the electrical charge generated by contact between the first and second materials, and a switch electrically coupled between one of the first and second surfaces and the energy storage device;

repeatedly moving the first and second surfaces together and apart; and cyclically opening and closing the switch.

19. The method of claim 18, wherein cyclically opening and closing the switch comprises:

opening and closing the switch at a predetermined frequency.

20. The method of claim 18, wherein cyclically opening and closing the switch comprises:

opening the switch when the first and second surfaces press together; and closing the switch when the first and second surfaces are furthest apart.

* * * * *